United States Patent
Kraus et al.

(10) Patent No.: US 6,632,599 B1
(45) Date of Patent: *Oct. 14, 2003

(54) DETECTION AND DETERMINATION OF SOLID PHASE-ASSOCIATED FACTORS

(75) Inventors: Michael Kraus, Marburg (DE); Carsten Schelp, Marburg (DE); Wilhelm Schuy, Obererbach (DE)

(73) Assignee: Dade Behring Marburg GmbH, Marburg (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/215,209

(22) Filed: Dec. 18, 1998

(30) Foreign Application Priority Data

Dec. 19, 1997 (DE) .......................... 197 56 782

(51) Int. Cl.⁷ .......................... C12Q 1/00; G01N 33/53; G01N 33/48; G01N 21/76
(52) U.S. Cl. .............. 435/4; 435/6; 435/7.24; 435/7.2; 435/7.31; 435/7.9; 435/962; 435/968; 435/13; 435/77; 435/7.92; 435/810; 436/63; 436/69; 436/172; 436/501; 436/519; 436/548; 252/700
(58) Field of Search .................. 435/4, 5, 6, 7.1, 435/7.2, 7.21, 7.24, 7.31, 7.9, 7.92, 7.23, 7.32, 7.34, 13, 77, 810, 961, 962, 968; 436/69, 63, 64, 172, 501, 519, 545, 546, 548, 521, 829; 252/700

(56) References Cited

U.S. PATENT DOCUMENTS 3,996,345 A  12/1976  Ullman et al. ............ 424/12
4,497,899 A   2/1985  Armstrong et al. ....... 436/510
5,047,321 A * 9/1991  Loken et al. .............. 435/6

(List continued on next page.)

FOREIGN PATENT DOCUMENTS

EP  0 371 049   6/1990
EP  0 392 865  10/1990

(List continued on next page.)

OTHER PUBLICATIONS

Guo, C. et al., "Fluorescence Resonance Energy Transfer Reveals Interleukin (IL)–1–dependent Aggregation of IL–1 Type I Receptors that Correlates with Receptor Activation," *Jour. Biol. Chem.*, vol. 27, No. 46, Nov. 1995, pp. 27562–27568.

Kosch, M. et al., "Fluorescence resonance energy transfer as a new method for the epitope–specific characterization of anti–platelet antibodies," *Jour. Immun. Methods*, 187 (1995) 53–67.

(List continued on next page.)

*Primary Examiner*—Long V. Le
*Assistant Examiner*—Changhwa J Cheu
(74) *Attorney, Agent, or Firm*—Finnegan, Henderson, Farabow, Garrett and Dunner, L.L.P.

(57) ABSTRACT

The present invention relates to procedures for the detection or for the determination of solid phase-associated factors, which are multiply associated with the same solid phase. According to the invention, the sample is brought into contact with a transmitter particle, on which at least one ligand having binding affinity for a solid phase-associated factor and a transmitter are immobilized, and a receiver particle, on which at least one ligand having binding affinity for said solid phase-associated factor and a receiver is immobilized, and then the signal is determined which results when transmitter and receiver are brought sufficiently close to one another. In particular, the invention relates to the detection of cell surface receptors which can be used for the typing of cells or for the determination of cell activation states. It is thus possible to replace the hitherto widely customary flow cytometry by a more simple procedure.

29 Claims, 1 Drawing Sheet

U.S. PATENT DOCUMENTS

| | | | |
|---|---|---|---|
| 5,340,716 A | * | 8/1994 | Ullman et al. .................. 435/6 |
| 5,527,684 A | | 6/1996 | Mabile et al. ................ 435/7.1 |
| 5,536,642 A | * | 7/1996 | Barbera-Guillem et al. .......................... 435/7.23 |
| 5,552,290 A | | 9/1996 | Michelson et al. ......... 435/7.21 |
| 5,709,994 A | * | 1/1998 | Pease et al. .................... 435/4 |

FOREIGN PATENT DOCUMENTS

| | | |
|---|---|---|
| EP | 0 402 396 | 12/1990 |
| EP | 0 444 303 | 9/1991 |
| EP | 0 451 687 | 10/1991 |
| EP | 0 515 194 | 11/1992 |
| EP | 0 515 194 A2 | 11/1992 |
| WO | WO 95/06877 | 3/1995 |

OTHER PUBLICATIONS

Kubitscheck, Ulrich et al., "Fluorescence resonance energy transfer on single living cells, Application to binding of monovalent haptens to cell–bound immunoglobulin E," *Biophysical Journal*, vol. 60, Aug. 1991, pp. 307–318.

Damianovich, Sandor et al., "Preassembly of interleukin 2 (IL–2) receptor subunits on resting Kit 225 K6 T cells and their modulation by IL–2, IL–7, and IL–15: A fluorescence resonance energy transfer study," *Proc. Natl. Acad. Sci.*, vol. 94, Nov. 1997, pp. 13134–13139.

Szollosi, J. et al., "Application of Fluorescence Resonance Energy Transfer in the Clinical Laboratory: Routine and Research," *Cytometry*, 34:159–179 (1998).

Yegneswaran, S. et al., "Protein S Alters the Active Site Location of Activated Protein C above the Membrane Surface," *Jour. Biol. Chem.*, vol. 272, No. 40, Oct. 1997, pp. 25013–25021.

European Search Report, Apr. 5, 2000.

R. Hynes, "Integrins: A Family of Cell Surface Receptors", Cell, 48:549–554 (1987).

M.P. Bevilacqua et al., "Endothelial–Leukocyte Adhesion Molecules in Inflammation and Metastasis", Thromb. Haemost., 70:152–154 (1993).

K.J. Clemetson, "Biochemistry of Platelet Membrane Glycoproteins", Prog. Clin. Biol. Res., 283:33–75 (1988).

J. Römisch et al., "Anticoagulant Properties of Placenta Protein 4 (Annexin V)", Throm. Res., 60:355–366 (1990).

H. Hart et al., "Scintillation Proximity Assay (SPA)–A New Method of Immunoassay", Molecular Immunology, 16:265–267, (1979).

S. Udenfriend et al., "Scintillation Proximity Radioimmunoassay Utilizing $^{125}$I–Labeled Ligands", Proc. Natl. Acad. Sci., 82:8672–8676 (1985).

E. Ullman et al., "Luminescent Oxygen Channeling Immunoassay: Measurement of Particle Binding Kinetics By Chemiluminescence", Proc. Natl. Acad. Sci., 91:5426–5430 (1994).

E. Ullman et al., "Luminescent oxygen Channeling Assay (LOC™): Sensitive, Broadly Applicable homogeneous Immunoassay Method", Clinical Chemistry, 42:1518–1526 (1996).

S. Bystryak et al. "A Homogeneous Immunoflurescence Assay Based on Dye–Sensitized Photobleaching", Analytical Biochemistry, 225:127–134 (1995).

G. Mathis, "Rare Earth Cryptates and Homogeneous Fluoroimmunoassays with Human Sera", Clin. Chem., 39:1953–1959 (1993).

* cited by examiner

Identical antibodies on transmitter and receiver particles

Different antibodies on transmitter and receiver particles

DETECTION AND DETERMINATION OF SOLID PHASE-ASSOCIATED FACTORS

BACKGROUND OF THE INVENTION

The present invention relates to procedures for the detection or for the determination of solid phase-associated factors, which are multiply associated with the same solid phase. According to the invention, the sample is brought into contact with a transmitter particle, on which at least one ligand having binding affinity for a solid phase-associated factor and a transmitter are immobilized, and a receiver particle, on which at least one ligand having binding affinity for said solid phase-associated factor and a receiver is immobilized, and then the signal is determined which results when transmitter and receiver are brought sufficiently close to one another. In particular, the invention relates to the detection of cell surface receptors which can be used for the typing of cells or for the determination of cell activation states. It is thus possible to replace the hitherto widely customary flow cytometry by a more simple procedure.

The differentiation of blood cells, in particular of leucocytes granulocytes, monocytes and lymphocytes) is a routinely used and important procedure in diagnostics. It is based, inter alia, on the fact that different cell types are characterized by different surface antigens, such as, for example, membrane proteins of the integrins family (Hynes R O. Integrins: a family of cell surface receptors. Cell 1987; 48: 549–554) (incorporated herein by reference). Most of these membrane proteins are designated by CD numbers (cluster designation numbers).

Membrane proteins can also only be exposed on the surface after stimulation of the cells or secreted by fusion of intracellular vesicles with the surface, such as, for example, proteins from the selectins group (Bevilacqua M P and Nelson R M. Endothelial-Leukocyte adhesion molecules in inflammation and metastasis. Thromb. Haemost. 1993; 70: 152–154) (incorporated herein by reference).

In the case of platelets, for example, GMP-140 (P selectin; DC62P) is an activation marker. Furthermore, in activation states characteristic complexes of receptors of cells and ligands can result, such as, for example, on activated platelet complexes of the glycoproteins GP Ib/IX or GP IIb/IIIa, which bind von Willebrand factor or fibrinogen (see, for example, Clemetson K J. Biochemistry of platelet membrane glycoproteins, Prog. Clin. Biol. Res. 1988; 283:33–75) (incorporated herein by reference). After activation, phosphatidylserine-containing lipid membranes, to which clotting factors or other phospholipid-binding protein (for example from the annexins family) can bind, are also exposed on platelets.

In previous procedures, labeled antibodies or other labeled reactive ligands, for example annexins, against these surface antigens were added to blood for the detection of phosphatidylserine-containing lipid membranes (Römisch J et al., Anticoagulant properties of placenta protein 4 (annexin V); Thromb. Res. 1990; 60: 355–366) (incorporated herein by reference). By means of flow cytometry, the cells are then sorted according to their size and in the course of this a conclusion is drawn at the same time via the detection of the labeling on the number and proportions of one or several cell types in parallel. Labels used are substances known per se to the person skilled in the art, in particular chemiluminescent compounds (for a general survey see, for example, Michelson, A. D. and Barnard, M. R., U.S. Pat. No. 5,552,290) (incorporated herein by reference).

The abovementioned flow cytometry is an established procedure, but has the disadvantage that it can be used only for the specific purpose of cell counting and/or typing. Usually, it is therefore also only established in specific laboratories. Wider use of the differentiation of cells and their activation states would be desirable, however, for clinical problems. For routine use, application in customary clinicochemical analyzers or other automated equipment is necessary for the routine laboratory.

The invention was therefore based on the object of making available an alternative to the previously customary flow cytometry methods, which allows the determination of cell surface antigens in a homogeneous, immunochemical procedure.

A number of homogeneous, immunochemical procedures for the determination of antigens and antibodies are already known, such as, for example, the FRAT[1] System (Syva), the EMIT[1] System, enzyme channeling immunoassays, fluorescence energy transfer immunoassays (FETI, e.g. TRACE[1] Technology; CIS bio International), enzyme inhibitor immunoassays (Hoffmann LaRoche, Abbott Laboratories) or fluorescence polarization immunoassays (Dandlicker). These homogeneous procedures were developed in order to offer methods which can be carried out without separation and/or washing steps. Some of these procedures have only a limited sensitivity or are not suitable for the determination of high molecular weight analytes having multiple epitopes.

The expression scintillation proximity assay (SPA) was introduced by Hiram E. Hart and Elaine B. Greenwald (Molecular Immunology 1979; 16: 265–267) (incorporated herein by reference) in order to describe a specific homogeneous radioimmunoassay. In this procedure, two different types of polymeric beads are employed, which are loaded with specific binding components. The first of these bead types is additionally loaded with a dye while the second bead type additionally carries tritium. The dye has the property of emitting light pulses as soon as it is stimulated by the $^1$H β-radiation (Auger electrons). This radiation, however, only has a range of a few micrometers in aqueous solutions, so that in dilute suspensions which contain both bead types, only a few beads of the one type are found in sufficiently close to beads of the other type. As a result, all in all only a small fluorescence signal can result. By means of the addition of reactants which can react with the specific binding components of the two bead types, however, an aggregation of the beads takes place which brings many of the beads of the first type (tritium beads) into the vicinity of beads of the second type (fluorophore beads), so that an altogether higher signal results. The resulting signal is detected in a scintillation counter. A further development of this procedure by use of $^{125}$iodine-labeled specific binding components was described by Udenfriend, S. et al. (Proc. Natl. Acad. Sci. 1985; 82: 8672–8676) (incorporated herein by reference).

A further procedure is described (EP-0 515 194 A2; Ullman et al., Proc. Natl. Acad. Sci. 1994; 91: 5426–5430 (incorporated herein by reference); Ullman et al., Clinical Chemistry 1996; 42: 1518–1526) (incorporated herein by reference) as a luminescent oxygen channeling immunoassay (LOCI). In this, two particle types are used, one of which contains a photosensitizer (sensitizer beads) and the other a chemiluminescent component (acceptor beads). The photosensitizer generates singlet oxygen and activates the chemiluminescent component if it is sufficiently close. The activated chemiluminescent component generates light which can be detected as a measuring signal.

Bystrak, S. et al. (Analytical Biochemistry 1995; 225: 127–134) (incorporated herein by reference) describe a homogeneous procedure in which a photooxidation of a fluorescent substrate, which is bonded to a unilaminar vesicle, by singlet oxygen takes place. Specific binding components are covalently bound to the surface of the vesicle.

These procedures all comprise specific binding of particles to binding components. As a rule, the binding of these binding components is carried out via the coating of the particles with appropriate specific ligands, such as, for example, antigens or antibodies for immunochemical detection. Up to now, these procedures were only used for the detection of soluble (humoral) factors. On binding to these factors (for example proteins), transmitter and receiver particles are brought into a spatial vicinity which allows a transfer of the energy emitted by a transmitter to a receiver particle. Use for the detection of insoluble, solid phase-associated factors, such as, for example, cell surface antigens, has not previously been pointed out.

SUMMARY OF THE INVENTION

Surprisingly, it was found in the context of the present invention that transmitter and receiver particles can be bound to a solid phase-associated factor which is multiply solid phase-associated such that the spatial vicinity necessary for the energy transfer is achieved independently of the size of the solid phase or, in other words, that the greatest distance between transmitter particles and receiver particles at which energy transfer can still take place is not exceeded. The solid phase can be, for example, a cell and the solid phase-associated factor can be, for example, a cell surface antigen. Surprisingly, it was thus possible to show that the extension of homogeneous immunochemical detection procedures, which until now were limited exclusively to the detection of humoral factors, to the detection of cell surface markers is possible, so that their determination can also be carried out in equipment based on a principle other than that of flow cytometry.

The present invention therefore relates to a procedure for the detection or for the determination of a solid phase-associated factor F, which is multiply associated with the same solid phase, in a sample. According to the invention, the sample is brought into contact with a first stable complex, consisting of at least one ligand L, which has binding affinity for F, and a transmitter T, as well as a second stable complex, consisting of at least one ligand L, which has binding affinity for F, and a receiver R, such that complexes F-L-T and F-L-R are formed. The signal is determined which results when T and R are sufficiently close to one another.

The present invention additionally relates to a procedure for the simultaneous detection or for the simultaneous determination of at least one first solid phase-associated factor Fx and a second solid phase-associated factor Fy, where Fx and Fy are associated with the same solid phase, in a sample. According to the invention, the sample is brought into contact with at least one first stable complex, consisting of at least one ligand Lx which has binding affinity for Fx, and a transmitter T, and also a second stable complex, consisting of at least one ligand Ly which has binding affinity for Fy, and a receiver R, such that complexes Fx-Lx-T and Fy-Ly-R are formed. The signal is determined which results when T and R are sufficiently close to one another.

According to a preferred embodiment, the stable complexes L-T, L-R, Lx-T or Ly-R comprise in each case particles, L or Lx being immobilized together with T on a first particle and L or Ly being immobilized together with R on a second particle.

More preferably, the solid phase is a cell, for example an erythrocyte, leucocyte, granulocyte, lymphocyte, monocyte, thrombocyte, or a cell from another tissue or organ. According to the invention, however, the term cell can also mean a prokaryotic or eukaryotic exogenous cell, such as a bacterium or parasite, or alternatively a subcellular parasite, for example a virus.

Solid phase-associated factors are to be understood as meaning both factors which are integrated into the solid phase and those factors which are not integrated into the solid phase, but are associated with it on account of other interactions.

A possible sample material is, for example, body fluid, tissue extract or ex-vivo cultures. Body fluids here are preferably blood, synovial fluid, cerebrospinal fluid, ascites or urine, particularly preferably whole blood or platelet-rich plasma.

The present invention furthermore relates to a procedure in which F, Fx and/or Fy is an integral membrane protein, a membrane-associated protein, a glycostructure or a lipid. The integral membrane protein can in this case be, for example, an integrin, selectin, a protein from the MHC complex or another known protein according to the cluster designation. Membrane-associated proteins are not integrated into the membrane, but detectable on the surface via specific ligand/receptor interactions, such as, for example, fibrinogen on fibrinogen receptors, antibodies against membrane proteins, complement factors or lectins against carbohydrate structures on the membrane surface and/or membrane proteins or processed antigen in the MHC complex on antigen-presenting cells. The membrane-associated proteins are furthermore proteins which are detectable on the surface via electrostatic interactions, such as, for example, active enzymes of the clotting system or proteins from the annexins family. The lipids according to the invention are substances known to the person skilled in the art from the acylglycerols, phosphoglycerides, sphingolipids, waxes, terpenes, steroids and/or prostaglandins group. According to the invention, the composition of the phospholipids of the surface membrane, such as, for example, the proportion of phosphatidylserine or of phosphatidylethanolamine, is preferentially detected by binding affinitive ligands, such as proteins from the annexins family, or by binding affinitive proteins of the clotting system such as, for example, activated protein C or protein S.

The present invention additionally relates to procedures in which the ligand binds to F, Fx or Fy via a mediatory binding component.

The present invention furthermore relates to procedures in which L, Lx or Ly is bound to particles via a biotin-avidin bridge.

The present invention moreover relates to procedures in which L, Lx or Ly can be an antibody, antigen, lectin, coenzyme, apoprotein, ligand of a receptor, substrate analog or annexin.

According to a preferred embodiment of the present invention, an energy transfer takes place between the transmitter T and the receiver R. This can be effected, for example, by radioactive processes, or by excitation of photosensitive dyes and direct or indirect electron transfer caused thereby, for example by means of activated oxygen. According to a further embodiment of the present invention, the energy transfer in the receiver particle leads to a reaction, for example an emission of luminescence, preferentially chemiluminescence, or fluorescence, which is detectable and a measure of the spatial vicinity of transmitter and receiver particles.

According to the invention, it is also possible by the addition of the substances modulating energy transfer known to the person skilled in the art in the particular system, for example damping substances, such as, for example, dyes or antioxidants, to decrease the minimum distance necessary between transmitter and receiver particle and thus to improve the measurement/background signal ratio.

The procedure according to the invention can be used, for example, for the characterization of cell types, subgroups or activation states of cells, and the detection of surface markers or surface antigens, for example neoepitopes in the context of tumor formation on cells. It can also be used for the typing of tissues or the characterization of tissue compatibility. In particular, the present invention also relates to the identification of exogenous cells, generally pathogens, such as bacteria. The process according to the invention is very particularly suitable for the identification of chlamydia.

"Transmitter" and "receiver" in the context of the present invention are understood as meaning members of classes of biological or chemical substance which can interact with one another in spatial vicinity, e.g. in the form of energy donors and energy recipients, such as, for example, photosensitizers and chemiluminescers (EP-0 515 194; Ullman et al. (1996) Clinical Chemistry 42:1518–1526), photosensitizers and fluorophores (WO 95/06877; Bystrak et al. (1995) Anal. Biochem. 225:127–134), or radioactive iodine$^{125}$ and fluorophores (S. Udenfriend et al. (1985) Proc. Natl. Acad. Sci. 82:8672–8676), or fluorophores and fluorophores (Mathis, G. (1993) Clin. Chem. 39:1953–1959) or fluorophores and fluorescence quenchers (U.S. Pat. No. 3,996,345) each of which is incorporated herein by reference. The energy transfer can in this case take place from one substance to another, whilst a cascade of various substances through which the energy transfer runs is also possible.

An interaction between transmitter and receiver is, in particular, an energy transfer —i.e. the direct transfer of energy between transmitter and receiver, for example by means of light or electron radiation, and also by means of reactive chemical molecules.

In addition, the idea of an interaction between transmitter and receiver is also understood as meaning enzyme cascades. In this case, the substances are enzymes, of which at least one yields the substrate for another.

Also included in this are processes in which the activity of a substance is inhibited or increased by one or more others, for example the inhibition of or increase in enzyme activity or the inhibition of, increase in or change (e.g. wavelength shift) in the light emitted by the affected substance.

An effective interaction between transmitter and receiver takes place when these are spatially adjacent, i.e., for example, within a distance range of a few $\mu$m, in particular within a distance range of less than 600 nm, preferably less than 400 nm, very particularly preferably less than 200 nm.

In a preferred embodiment of the procedure according to the invention, the interaction between transmitter and receiver is effected as an energy transfer, e.g. by means of the following methods, the references to which are incorporated herein by reference:

short-lived molecules, e.g. singlet oxygen (see also EP 0 515 194; Ullman et al. (1994) Proc. Natl. Acad. Sci. 91:5426–5430; Ullman et al. (1996) Clinical Chemistry 42:1518–1526, WO 95/06877 and Bystrak et al. (1995) Anal. Biochem. 225: 127–134), radiation of low range, e.g. radioactive β-radiation (see Hart & Greenwald (1979) Molecular Immunology 16:265–267 and Udenfriend et al. (1985) Proc. Natl. Acad. Sci. 82:8672–8676), and/or energy transfer according to Förster (Mathis, G. (1993) Clin. Chem. 39:1953–1959; U.S. Pat. No. 5,527, 684).

Included by the procedure according to the invention are also embodiments in which the surface of the particles has been further modified after their preparation and/or the particles are covered by one or more covalently or adsorptively bound layers or shells, for example of proteins, carbohydrates, lipophilic substances, biopolymers, organic polymers or mixtures thereof, in order, for example, to achieve improvements with respect to suspension stability, storage stability, shaping stability or resistance to UV light, microbes or other agents having a destructive action. The modifications and coverings can likewise be used here to reduce or to suppress the nonspecific binding to surfaces of reaction vessels and to those of protein constituents such as, in particular, proteins (e.g. albumin or antibody) or cell constituents (for example phospholipids or nucleic acids). Furthermore, the modifications and coverings are used to increase or to lower the hydrophobicity of the particle surface or the loading of the surface of the particles.

A further embodiment of the process according to the invention comprises employing, as transmitters or receivers, photosensitizers, for example acetone, benzophenone, 9-thioxanthone, eosin, 9,10-dibromoanthracene, chlorophyll, Buckminsterfullerene, Methylene Blue, Rose Bengal, porphyrins, phthalocyanines and/or their derivatives, and as chemiluminescent compounds, for example, olefins, 9-alkylidenexanthans, 9-alkylidene-N-alkylacridans, enol ethers, enamines, aryl vinyl ethers, dioxenes, arylimidazoles and/or lucigenin and it being possible for the singlet oxygen generated by the photosensitizer to activate the chemiluminescent compounds to emit light. Also preferred in the process according to the invention is the use of substances such as, for example, luminol and oxalate esters which react with singlet oxygen to give intermediates which can react with reagents known to the person skilled in the art with radiation of light.

As a rule, the chemiluminescent compounds emit light in the wavelength ranges over 300 nm. The fluorescence of plasma falls rapidly in the range from 500 nm and can be neglected above 550 nm. If higher wavelengths are required, the chemiluminescent compounds according to the invention can also be brought into contact with fluorophores which can be excited by the activated chemiluminescent compounds and emit at higher wavelengths. Suitable fluorophores are, for example, rhodamine, ethidium bromide, 5-dimethylaminonaphthalene-1-sulfonyl, europium chelates with the agent 3-(2-thienoyl)-1,1,1-trifluoroacetone [Eu (TTA)$_3$ (TTA=3-(2-thienoyl)-1,1,1-trifluoroacetone)] or ruthenium chelates with the agent 2,2'-dipyridyl [Ru(bpy)$_3^{++}$(bpy=2,2'-dipyridyl)].

A further embodiment of the procedure according to the invention comprises employing photosensitizers and fluorescent compounds as substances and it being possible for the fluorescent compound for light emission to activate or, in a quench process, to suppress the light emission of the singlet oxygen generated by the photosensitizer. In particular, procedures according to the invention are preferred which comprise the use of fluorescent compounds which are subject to photooxidation—photobleaching—by reaction with singlet oxygen, such as, for example, 1,3-diphenylisobenzofuran, or react with singlet oxygen as photoactive precursors to give fluorophores, such as, for example, oxene umbelliferyl ethers or umbelliferyl selenides.

With respect to further examples of particles, photosensitizers, chemiluminescent or fluorescent compounds suitable for the procedure according to the invention, reference is made, in particular, to EP 0 515 194, Ullman et al. (Proc. Natl. Acad. Sci. 91:5426–5430, 1994) and Ullman et al. (Clinical Chemistry 42:1518–1526, 1996, WO 95/06877) each of which are specifically incorporated by reference.

DETAILED DESCRIPTION OF THE INVENTION

Since a solid phase in the sense of the present invention, for example a cell, can be considered as polyvalent with respect to a solid phase-associated factor, for example a surface epitope, two different binding components do not necessarily have to be applied to transmitter and receiver particles. The same binding component on transmitter and receiver particles is thus sufficient for the detection of certain solid phase-bound factors, for example of antigens or ligands. The determination of certain cell types or the determination of certain activation states which accompany the expression of certain factors on the cell surface is thus made possible.

Moreover, it is also possible, however, to apply two or more different binding components to transmitter and receiver particles in order additionally to allow further differentiations for the detection of individual factors, such as, for example, of individual antigens. To do this, however, the radius of the effective energy transfer must be so low that it can really only take place between very closely adjacent transmitter and receiver particles and the polyvalence of the solid phase itself—for example on account of the great accummulation of one of the binding components, leads to no undesired energy transfer. The radius of the effective energy transfer is dependent on the detection system used, and the reduction of this radius can be achieved by altering the nature of the particles or affecting the quench effect of the surrounding solution by means of additives known to the person skilled in the art.

Figure 1A:
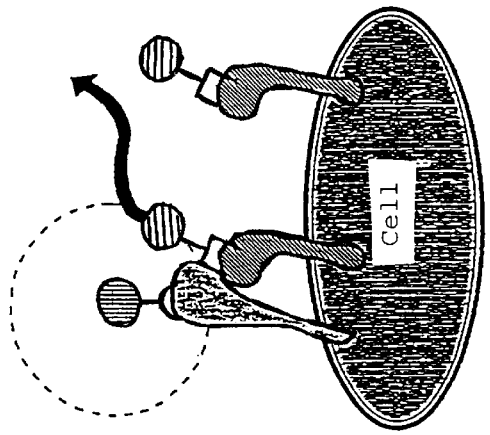
FIG. 1A illustrates identical antibodies on transmitter and receiver particles.
Figure 1B:
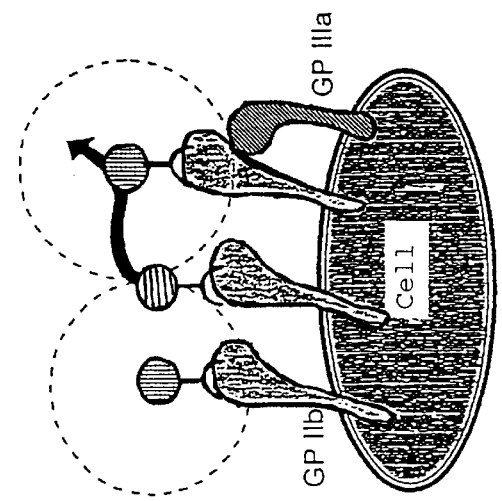
FIG. 1B illustrates different antibodies on transmitter and receiver particles.
Figure 1B:
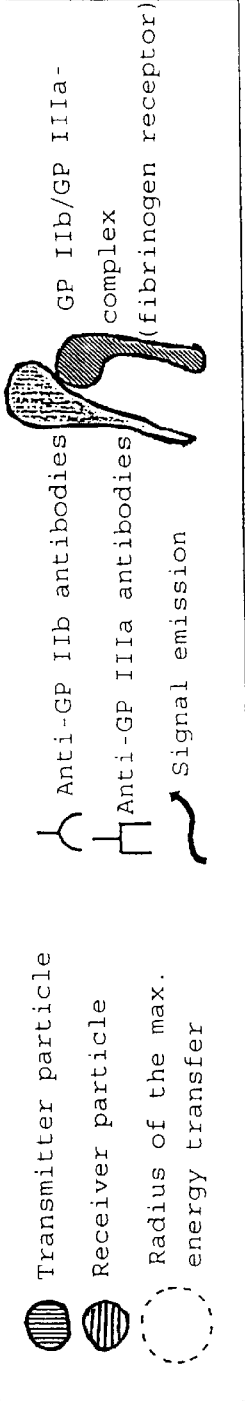

Reference is made to FIG. 1 for closer, exemplary explanation. According to FIG. 1A, transmitter and receiver particles were loaded with the same antibody against GP IIb. A transfer of the energy from the transmitter to the receiver and thus a signal emission only occurs when the GP IIb molecules are so densely arranged on the cell surface that the average distance of the molecules from one another is smaller than the maximum radius within which energy transfer between transmitter and receiver particles is still possible. Under these circumstances, signal transmission is a measure of the quantity (the frequency on the surface) of a certain surface epitope, in the present example of GP IIb.

Of interest, for example, is the determination of individual surface antigens, such as T4 and T8 for the differentiation of lymphocytes, IgE receptors for the detection of allergic reactions, or the determination of histocompatibility antigens in cell extracts or lyzates before transplantation of organs or tissues, or the diagnosis of cell activation states by the detection of changes in consecutive or newly presented integral membrane proteins, of surface-active proteins or of neoepitopes.

If transmitter and receiver particles, as shown in FIG. 1B, are loaded with two different ligands, for example the transmitter with antibodies against GP IIb and the receiver with antibodies against GP IIIa, then a signal is only generated when the two different ligands are sufficiently close to one another, i.e. in the present example when the complete fibrinogen receptor GP IIb/IIIa is present on the cell.

Other complexes whose detection is of interest can consist, for example, of the following components: of clotting enzymes and their cofactors, or of clotting enzymes and physiologically active surfaces, or of components of the MHC (major histocompatibility complex), or of T3, Tr and T4 or T8 on immune cells, or of components of the complement system, such as, for example, the MAC (membrane attack complex), consisting of the complement factors C5b, C6, C7, C8, C9 and vitronectin (T protein). In the last case, it is conceivable, for example, to measure the current lysis activity of the complement system by using antibodies against C9 on their own or combinations of antibodies against two or more of these components; for example it is possible by this means to differentiate the completeness of the complex formation (e.g. C5b–C6, C5b–C7, C5b–C8, C5b–C9).

The process according to the invention can also be used for simplifying the detection of microorganisms. In the following, the principle of the present invention is illustrated as exemplified by chlamydia detection, it being immediately clear to the person skilled in the art that the invention is not limited to the detection of this microorganism.

A multiplicity of methods for the detection of chlamydia has already been described, such as, for example, the culturing of chlamydia in cell cultures, immunoassays or nucleic acid (DNA detection procedures). The immunological test procedures are aimed, for example, at the specific detection of chlamydia for making a clinical diagnosis. Two methods have essentially been used here: a first in which enzyme-labeled antibodies were measured in the chlamydia antigen released beforehand; a second in which chlamydia fixed to slides were detected microscopically by means of fluorescence-labeled antibodies using unliberated antigen still bound to chlamydia.

For all procedures known up to now, several steps which take place during a sample preparation for the test or in the test are necessary. Some should be mentioned below: in preparation for the test, the chlamydia antigens to be detected must be extracted. This is carried out with the aid of detergents (see, for example, EP-0 392 865) (incorporated herein by reference) or with the aid of detergents under simultaneous alkaline conditions (see, for example, EP-0 402 396) (incorporated herein by reference). Other processes need, optionally additionally to the extraction, washing steps during the course of the test in order to remove unbound chlamydia-specific antibodies (see, for example, U.S. Pat. No. 4,497,899) (incorporated herein by reference).

A further previously known procedure necessitates heating to 100° C. for 15 min in order to release chlamydia-specific antigens for detection (EP-0 371 049) (incorporated herein by reference). Other different procedures extract antigens, form immune complexes, which then have to be filtered off for detection, via specific antibodies, followed by washing steps to remove unbound antibodies (EP-0 451 687) (incorporated herein by reference). A further previously known process transports enzymatically released antigens through a porous membrane in which chlamydia-specific antibodies bind to the released antigens and are detected by means of subsequent steps (EP-0 444 303) (incorporated herein by reference).

It has additionally been found that by use of LOCI technology immunochemically insoluble antigens can be detected directly on the chlamydia cells without prior release. It is sufficient to disperse chlamydia cells in a buffer and to bind transmitter and receiver particles immunochemically in an aliquot of this cell suspension and to measure the signal without a further washing step. Since the two different antibodies recognise different structural constituents in a chlamydia cell, for detection according to the invention formation of a signal can only be induced if both— transmitter and receiver particle—can be bound next to one another on a chlamydia cell. At the same time, this means that the chlamydia cell structure no longer has to be destructured in a time-consuming manner and the desired antigens extracted in order that the individual constituents of the chlamydia cell structure can be detected as in other test procedures (see Example 1). In addition to the reduction in expenditure of effort involved and sources of error, this also allows application to routine equipment, which on the basis of the pretreatment was previously not possible.

The present invention therefore also relates to a procedure according to which chlamydia cells contained in a sample are brought into contact with transmitter and receiver particles, both types of particles in each case carrying at least one ligand having binding affinity for chlamydia cells and the transmitter particles additionally carrying a transmitter and the receiver particles additionally carrying a receiver. The signal is then determined which results when transmitter and receiver are brought sufficiently close to one another.

The following examples are intended to further illustrate the present invention, but not to restrict it. As an example of a homogeneous, immunochemical procedure, LOCI technology was selected.

EXAMPLE

Detection of Surface Antigens of Chlamydia in Suspension

As transmitter and receiver particles, sensitizer and chemiluminescer particles respectively were used according to LOCI technology. The particles were obtained from the Syva Business Unit, Behring Diagnostics Inc., San José. The preparation instructions followed the procedures described in EP Patent 0 515 194 and in the references Ullman et al. Clin Chem. (1996) 42:9, 1518–1526 and Natl. Acad. Sci. (1994) 91, 5426–5430. Acceptor particles were coated with a lipopolysaccharide (LPS)-specific antibody. The coating procedure is described in Ullman et al. (1996) 42:9, 1518–1526. Parallel to this, a specific antibody against the major outer membrane protein (MOMP) was labeled with biotin. Sensitizer particles were coated with avidin. These procedures are also described in Ullman et al. (1996) 42:9, 1518–1526 (incorporated herein by reference).

Before the test, the chlamydia, the acceptor beads, the biotinylated antibody and the sensitizers were diluted in the following buffer: 0.1 M tris HCl; 0.5 M NaCl; 0.025 M EDTA; 1.6% BTA (pH 7.6).

To carry out the test, the components were mixed and incubated as follows. The instrumentation necessary for this is described in Ullman et al. (1996) 42:9, 1518–1526.

25 μl of chlamydia suspension were mixed with 25 μl of acceptor beads (100 μg/ml) and incubated at 37° C. for 6 min. 35 μl of biotinylated antibodies (10 μg/ml) were then added and the mixture was again incubated at 37° C. for 6 min. 50 μl of sensitizer particles (400 μg/ml) were then added and the emitted chemoluminescence was determined in a luminometer.

For comparison, a test batch without Chlamydia was used.

The signals of the two batches were:

Signal with sample buffer (control): 8698 signal with chlamydia cells: 13221

What is claimed is:

1. A method for the simultaneous detection of the presence or amount of multiple cell-associated factors, which are associated with the same cell, said method comprising:

1) providing a sample containing a cell comprising at least one cell-associated factor $F_x$ and at least one cell-associated factor $F_y$;

2) selecting a receiver R and a transmitter T which enter into interaction with each other when in spatial proximity, and wherein the interaction directly or indirectly provides a signal;

3) providing at least one stable receiver complex, $L_x$-R, comprising the receiver R, and at least one ligand $L_x$, wherein $L_x$ has binding affinity for the at least one cell-associated factor $F_x$;

4) providing at least one stable transmitter complex, $L_y$-T, comprising the transmitter T, and at least one ligand $L_y$, wherein $L_y$ has binding affinity for the at least one cell-associated factor $F_y$;

5) contacting the sample with the at least one stable receiver complex and the at least one stable transmitter complex, wherein, in the presence of the at least one cell-associated factor $F_x$ and $F_y$, complexes $F_x$-$L_x$-R and $F_y$-$L_y$-T are formed and;

6) detecting a signal provided by the interaction of T and R, wherein the detection of the signal correlates with the detection of the presence or amount of multiple cell-associated factors.

2. The method as claimed in claim 1, wherein the transmitter complex is immobilized on a first particle and the receiver complex is immobilized on a second particle.

3. The method as claimed in claim 1, wherein the cell is selected from the group consisting of a blood cell, a cell from a tissue, and a cell from an organ.

4. The method of claim 3, wherein the cell is an erythrocyte, leucocyte, granulocyte, lymphocyte, monocyte, or thrombocyte.

5. The method of claim 1, wherein the cell is an exogenous cell.

6. The method of claim 1, wherein the cell is a bacterium, parasite, or virus.

7. The method of claim 1, wherein at least one of $F_x$ and $F_y$ is an integral membrane protein.

8. The method of claim 7, wherein the integral membrane protein is selected from the group consisting of integrins, selecting, and an MHC complex protein.

9. The method of claim 1, wherein at least one of $F_x$ and $F_y$ is a membrane-associated protein.

10. The method of claim 9, wherein the membrane-associated protein is selected from the group consisting of fibrinogen, an antibody, a complement factor, a lectin, a processed antigen in the MHC complex, an enzyme of the clotting system, and a protein from the annexins family.

11. The method of claim 1, wherein at least one of $F_x$ and $F_y$ is a lipid.

12. The method of claim 11, wherein the lipid is a derivative of a member selected from the group consisting of acylglycerols, phosphoglycerides, sphingolipids, waxes, terpenes, steroids, and prostaglandins.

13. The method of claim 11, wherein the lipid is a phospholipid and the at least one of $L_x$ and $L_y$ is a protein selected from the group consisting of the annexins family and a reactive protein of the clotting system.

14. The method of claim 11, wherein the lipid is selected from the group consisting of phosphatidylserine and phosphatidyl-ethanolamine and wherein the at least one of $L_x$ and $L_y$ is selected from the group consisting of protein C and protein S.

15. The method of claim 1, wherein at least one of the at least one ligand $L_x$ or $L_y$ binds to a factor via a mediatory binding component.

16. The method of claim 1, wherein at least one of the at least one ligand $L_x$ or $L_y$ is bound to a particle via a biotin-avidin bridge.

17. The method of claim 1, wherein the at least one of Lx and Ly is selected from the group consisting of antibody, lectin, coenzyme, apoprotein, ligand receptor, substrate analog, and annexin.

18. The method of claim 1, wherein the interaction between T and R comprises an energy transfer.

19. The method of claim 18, wherein the energy transfer comprises direct or indirect electron transfer.

20. The method of claim 19, wherein the direct or indirect electron transfer is the result of radioactive processes or the excitation of photosensitive dyes.

21. The method of claim 19, wherein the electron transfer is effected by activated oxygen.

22. The method of claim 18, wherein, the energy transfer produces luminescence, chemiluminescence, or fluorescence in the receiver complex.

23. The method of claim 1, wherein the signal is augmented, inhibited, or altered by a modulating substance.

24. The method of claim 1, wherein the signal is analyzed to characterize cell types, subgroups, or activation states of cells.

25. The method of claim 1, wherein at least one of Fx and Fy is a bacterial surface antigen.

26. The method of claim 1, wherein the signal is analyzed to identify pathogens.

27. The method of claim 26, wherein the pathogen is Chlamydia.

28. The method of claim 1, wherein at least one of $F_x$ and $F_y$ is a cell surface marker.

29. The method of claim 28, wherein the signal is analyzed for tissue typing or for tissue compatibility characterization.

* * * * *

UNITED STATES PATENT AND TRADEMARK OFFICE
CERTIFICATE OF CORRECTION

PATENT NO. : 6,632,599 B1
DATED : October 14, 2003
INVENTOR(S) : Michael Kraus et al.

Page 1 of 1

It is certified that error appears in the above-identified patent and that said Letters Patent is hereby corrected as shown below:

Column 10,
Line 62, "selecting," should read -- selectins, --.

Signed and Sealed this

Eighteenth Day of January, 2005

JON W. DUDAS
*Director of the United States Patent and Trademark Office*